(12) United States Patent
Pielli et al.

(10) Patent No.: US 9,128,034 B2
(45) Date of Patent: *Sep. 8, 2015

(54) MULTI-PROBE RAIL SCANNING/ENCODER SYSTEM AND CERTIFIED METHOD OF USE THEREOF

(75) Inventors: John A. Pielli, Jackson, NJ (US); Kenneth Gaglione, Franklin Park, NJ (US)

(73) Assignee: NATIONAL RAILROD PASSENGER CORPORATION, Washington, DC (US)

( * ) Notice: Subject to any disclaimer, the term of this patent is extended or adjusted under 35 U.S.C. 154(b) by 459 days.

This patent is subject to a terminal disclaimer.

(21) Appl. No.: 13/477,863

(22) Filed: May 22, 2012

(65) Prior Publication Data

US 2012/0227502 A1 Sep. 13, 2012

Related U.S. Application Data

(63) Continuation of application No. 12/356,356, filed on Jan. 20, 2009, now Pat. No. 8,196,469.

(51) Int. Cl.
*G01H 17/00* (2006.01)
*G01N 29/265* (2006.01)
*G01N 29/26* (2006.01)
*G01N 29/30* (2006.01)

(52) U.S. Cl.
CPC ............ *G01N 29/265* (2013.01); *G01N 29/262* (2013.01); *G01N 29/30* (2013.01); *G01N 2291/2623* (2013.01)

(58) Field of Classification Search
CPC .............. G01N 29/262; G01N 29/265; G01N 2291/2623; G01N 29/30
USPC ................... 73/584, 602, 633–634, 636, 639; 702/39, 104, 584
See application file for complete search history.

(56) References Cited

U.S. PATENT DOCUMENTS

| | | |
|---|---|---|
| 4,872,130 A | 10/1989 | Pagano |
| 5,392,659 A | 2/1995 | Ford, Jr. et al. |
| 5,419,196 A | 5/1995 | Havira et al. |
| 5,600,669 A | 2/1997 | Pieper |
| 5,619,423 A | 4/1997 | Scrantz |

(Continued)

FOREIGN PATENT DOCUMENTS

| | | |
|---|---|---|
| EP | 0096338 A2 | 12/1983 |
| EP | 0722085 A1 | 7/1996 |

(Continued)

OTHER PUBLICATIONS

Modification of Existing Paras make DRT for testing of rails for NBC and GFC testing simultaneously, Western Railway, GFC through testing Apr. 29, 2003.*

(Continued)

*Primary Examiner* — J M Saint Surin
(74) *Attorney, Agent, or Firm* — Lowe Hauptman & Ham, LLP

(57) ABSTRACT

A rail scanning system and certified method of use thereof are described. The rail scanning system comprises a control unit, a probe carriage, and an encoder. The probe carriage comprises two or more phased array probes. The control unit is communicatively coupled with the encoder and phased array probes of the probe carriage.

17 Claims, 10 Drawing Sheets

(56) References Cited

U.S. PATENT DOCUMENTS

| | | |
|---|---|---|
| 5,778,891 A | 7/1998 | McMahan |
| 6,594,591 B2 | 7/2003 | Clark et al. |
| 7,499,772 B2 | 3/2009 | Wilcox et al. |
| 8,196,469 B2 * | 6/2012 | Pielli et al. ............ 73/584 |
| 2006/0065055 A1 | 3/2006 | Barshinger et al. |
| 2006/0131464 A1 * | 6/2006 | Hesser et al. ......... 246/169 D |
| 2008/0127732 A1 | 6/2008 | Owens et al. |

FOREIGN PATENT DOCUMENTS

| | | |
|---|---|---|
| EP | 1394011 A1 | 3/2004 |
| WO | 82/03919 A1 | 11/1982 |

OTHER PUBLICATIONS

European Search Report of Application No. EP 10151174 mailed Jul. 5, 2010.

* cited by examiner

400

AMTRAK INSPECTION

| Date: | Type of Asset Being Tested |
|---|---|
| 20/06/2006 | Field Weld |
| Northeast Corridor Division | Rail / Frog / Special Location |
| Boston | North |
| Track Subdivsion | Milepost Location (1-200) |
| 1 | 100 |
| Track Number | Weld ID Number (1-300) |
| 1 | 152 |
| Tunnel Number | Name of Inspection (1-6) |
| 1 | 5 |

Accept

FIG. 4

MULTI-PROBE RAIL SCANNING/ENCODER SYSTEM AND CERTIFIED METHOD OF USE THEREOF

BACKGROUND

Conventional ultrasonic testing and phased array ultrasonic testing (UT) operating on similar principles. Both transmit sound waves which are transmitted through material via a transducer attached to a thermoplastic wedge shape at a specific angle (probe). The difference between them lies in the type of transducers used and how the information/data received is processed. In conventional UT, a single element transducer is used to transmit sound waves at a specified angle. Phased array UT uses a multiple element transducer which allows for a number of angles to be swept at one time.

DESCRIPTION OF THE DRAWINGS

One or more embodiments are illustrated by way of example, and not by limitation, in the figures of the accompanying drawings, wherein elements having the same reference numeral designations represent like elements throughout and wherein:

FIG. 4 is an exemplary dialog display according to an embodiment;

DETAILED DESCRIPTION

The Multi-Probe Rail Scanner/Encoder as designed allows for the testing of the subject area in one pass. All data compiled is recorded and saved for validation/certification and review. In at least some embodiments, validation/certification of the data only occurs if specific information is entered by the operator. The validated data is then transferred/transmitted to a computer at a field location. From the field location, the validated data is transferred/transmitted to a parent (central) location where the validated data is reviewed, analyzed and stored. In at least some embodiments, there are a minimum of 5 field locations. In at least some other embodiments, there are a greater or lesser number of field locations and/or a greater or lesser number of field locations.

Figure 1:
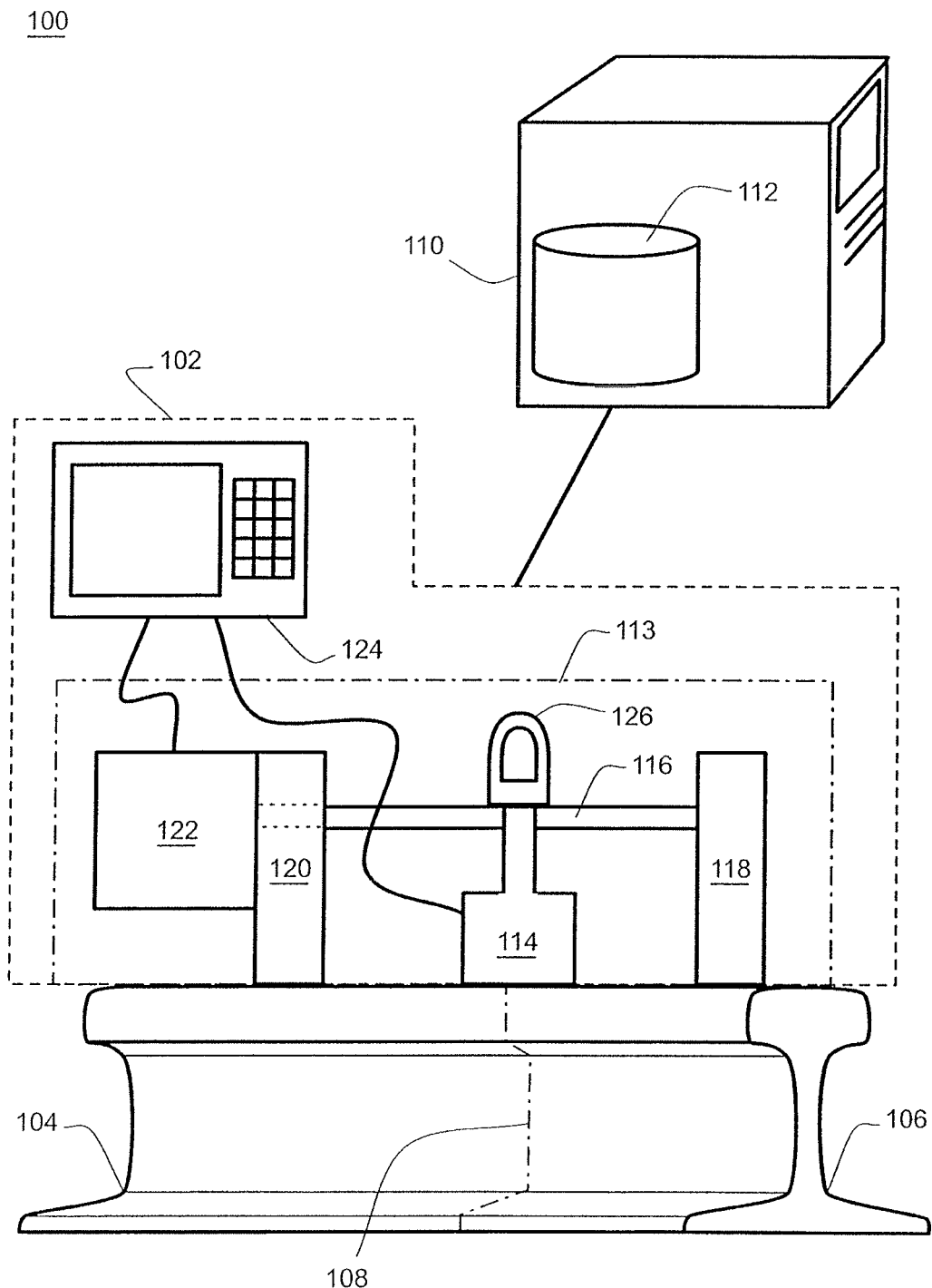
FIG. 1 is a high-level block diagram of an environment for using a rail scanning system according to an embodiment.

FIG. 1 depicts a high-level block diagram of an environment 100 for using a rail scanning system 102 according to an embodiment. Environment 100 comprises a pair of rail segments 104, 106 joined together at a joint 108 (indicated by dash-dot line). In at least some embodiments, joint 108 may be a welded or other type of joint joining two rail segments. In at least some embodiments, joint 108 may be formed by a welding process, e.g., flash butt, thermite reaction, or other welding process.

In at least some other embodiments, dash-dot line 108 indicates a region of a rail segment, e.g., either rail 104 or 106, identified for inspection.

In at least one embodiment of the present invention, a user manipulates rail scanning system 102 to scan a portion of rail, e.g., a region including joint 108 of rail segments 104, 106, using one or more phased array probes on a single carriage. The resulting scan information obtained may then be stored after specific identifying information related to the scan is entered by the user at the rail scanning system. In at least some embodiments, the identifying information comprises the date of the scan, a user identifier, and scan location information. In at least some embodiments, the resulting scan information also comprises scanner setting information related to the settings of the rail scanning system during the performed scan. In at least some embodiments, the resulting scan information is only stored after entry of the identifying information which is also stored.

In at least one embodiment of the present invention, rail scanning system 102 comprises a set of three phased array probes configured onto a single phased array probe carriage enabling a user to scan a portion of rail sweeping at more than one angle during a single scan. In at least some embodiments, the configured probes scan a portion of rail sweeping at multiple angles during a single scan. In at least some embodiments, the single phased array unit comprises three phased array probes on a single probe carriage configured to scan at an angle of zero (0°) degrees down the center of the rail head from the head to the base of the rail, between thirty-five and seventy degrees (35°-70°) down the rail head from the head to the base of the rail, and more than one, e.g., multiple angles, along the width of the rail head. Further details regarding the scans performed is provided below. In at least some embodiments, the three phased array probes on the probe carriage enable five (5) scans to be obtained (i.e., images of five different angles and/or portions of a rail portion) during execution of a single scan.

Rail scanning system 102 (indicated by dashed line) comprises several components communicatively and/or electronically coupled to generate and transmit a signal toward rail segments 104, 106 and a region of interest surrounding joint 108. Rail scanning system 102 receives response signals reflected by rail segments 104, 106 and/or the region of interest surrounding joint 108. In at least some embodiments, rail scanning system 102 generates one or more images of the material forming rail segments 104, 106 and/or joint 108. In at least some embodiments, rail scanning system 102 stores the received response signals in memory.

In at least some embodiments, rail scanning system 102 is moved along rail segments 104, 106 to cause the rail scanning system to scan, i.e., transmit signals and receive response signals, a portion of the rail segments, e.g., including joint 108. In at least some embodiments, a portion of rail scanning system 102, e.g., a probe carriage comprising phased array probes, scans a portion of the rail or rail segments by motion over the scanned area.

Images formed from the received response signals may be later analyzed to determine the presence/absence of defects in rail segments 104, 106 and/or joint 108.

Rail scanning system 102 is communicatively coupled to a computer system 110. In at least some embodiments, rail scanning system 102, and/or computer system 110 may comprise one or more wired and/or wireless interfaces and connections.

Rail scanning system 102 transmits the received response signals to computer system 110 for storage and/or analysis. Computer system 110 comprises a data store 112 for storing the received response signals from rail scanning system 102.

Rail scanning system 102 comprises a rail scanner 113 (indicated by dash-dot line) and a phased array unit 124. Rail scanner 113 comprises a phased array probe carriage 114 movably connected to a guide unit 116. Guide unit 116 connects between two end pieces 118, 120 which provide support for rail scanner 113 on rail segments 104, 106. In at least some embodiments, guide unit 116 comprises a threaded portion between end pieces 118, 120 which imparts a rotation to the guide unit during movement of phased array probe carriage 114 between end pieces 118, 120. For example, end piece 120 comprises a dashed line portion of guide unit 116 extending into the end piece sufficient to interact with encoder 122. Guide unit 116 is cooperatively coupled to encoder 122 and phased array probe carriage 114. In at least some embodiments, at least a portion of each of end pieces 118, 120 are magnetic to enable attachment of rail scanner 113 to rail segments 104, 106.

In at least some embodiments, a water-based or environmentally acceptable ultrasonic couplant is supplied between the phased array probes 114 and rail 104, 106. The couplant is a material having good wetting characteristics to transmit ultrasound from/to the phased array probes 114 elements to/from the rail. In at least some embodiments, the couplant is delivered to the rail by a couplant delivery system enabling the phased array probes 114 to slide across the surface of the rail during a scan. In at least some embodiments, couplant is delivered via throughholes and/or irrigation holes/openings to enable the introduction of the couplant to the rail surface. In at least some embodiments, the couplant is delivered to the rail in a pressurized manner.

In at least some embodiments, guide unit 116 is a minimum of 30 inches in length in order to enable scanning of a portion of rail which is at least 22 inches in length. In at least some embodiments, guide unit 116 may be longer or shorter length.

Rail scanner 113 also comprises an encoder 122 coupled to guide unit 116 and arranged to generate a motion signal indicative of the movement of phased array probe carriage 114 between end pieces 118, 120. In at least some embodiments, encoder 122 determines movement of phased array probe carriage 114 based on rotation of at least a portion of guide unit 116, e.g., rotation of the threaded portion interacting with the encoder. In at least some embodiments, encoder 122 determines movement of phased array probe carriage 114 based on movement of guide unit 116 in between end pieces 118, 120.

Rail scanning system 102 also comprises a control unit 124 communicatively coupled with rail scanner 113, i.e., encoder 122 and phased array probe carriage 114. An example control unit 124 is an OmniScan MX available from Olympus. Control unit 124 comprises a processing device such as a processor, microcontroller, application specific integrated circuit (ASIC) configured to perform specific functionality responsive to execution/interpretation of one or more instructions. Control unit 124 receives the generated motion signal from encoder 122 indicative of movement of the phased array probe carriage 114 and also receives the response signals received by the phased array probes. In at least some embodiments, control unit 124 receives the response signals directly from the phased array probes 114. In at least some embodiments, a three-way cable is used to connect phased array probes 114 to control unit 124. In at least some embodiments, control unit 124 receives a combined motion signal and response signal from encoder 122 where the encoder combines the motion signal with a received response signal from the phased array probes 114. In at least some embodiments, control unit 124 receives separately a motion signal from encoder 122 and a response signal from the phased array probes 114.

Control unit 124 transmits the received response signal(s) and motion signal(s) to computer system 110. In at least some embodiments, control unit 124 transmits the response signal and motion signal as a single file. In at least some embodiments, control unit 124 transmits the response signal and motion signal to computer system 110 responsive to user manipulation of the control unit. In at least some embodiments, control unit 124 transmits the response signal and motion signal to computer system 110 responsive to a determined connection established between the control unit and the computer system.

In at least some embodiments, a user transfers the response signal and motion signal by physically removing memory, e.g., a portable memory storage device, from control unit 124 and placing the memory into computer system 110.

In at least some embodiments, control unit 124 transmits the received response signal and motion signal responsive to a request received from computer system 110.

Control unit 124 comprises an input/output (I/O) device for displaying information to a user and/or for receiving commands and information from the user. Control unit 124 receives user-supplied input related to a user identifier and location identifying information. Control unit 124 stores scan setting information related to particular setting information of the control unit during a scan.

Rail scanning system 102, and in particular rail scanner 113, also comprises a handle 126 attached to phased array probe carriage 114 to allow a user to grasp and move the phased array probe carriage during a scan. In at least some embodiments, handle 126 may comprise different sizes and shapes to enable a user to move phased array probe carriage 114 between end pieces 118, 120.

Figure 2:
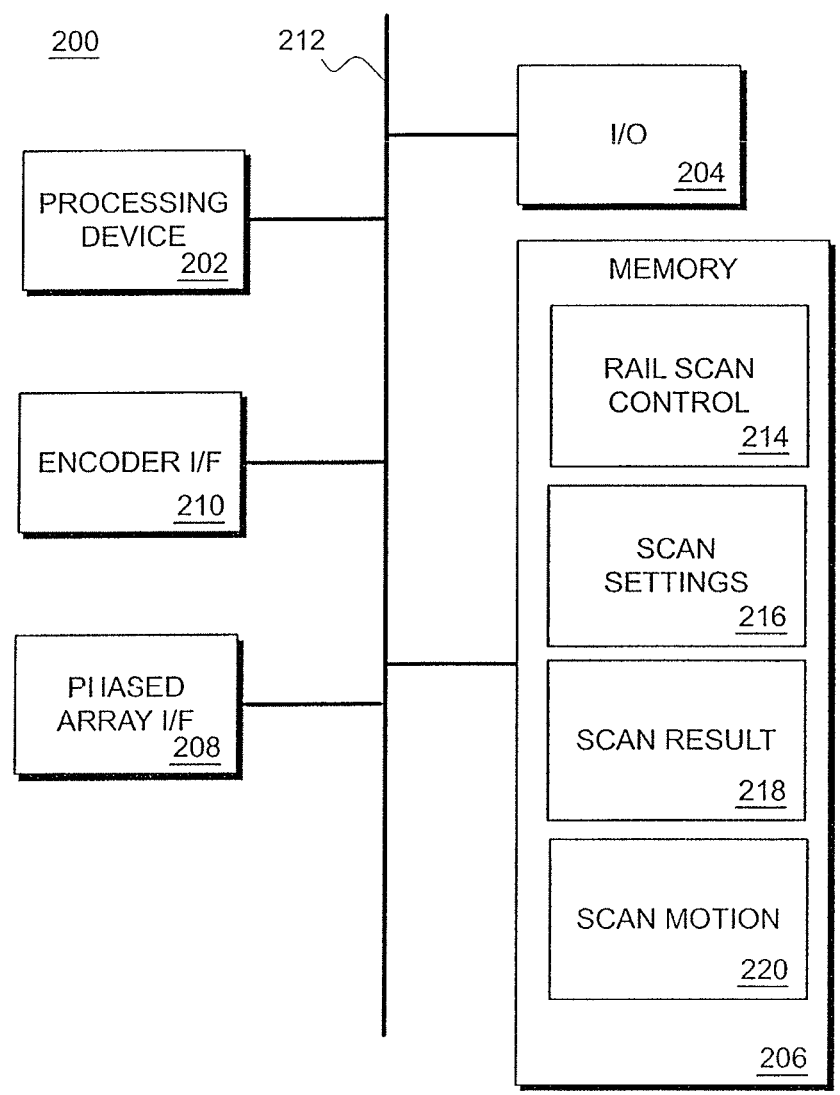
FIG. 2 is a high-level functional block diagram of a control unit according to an embodiment.

FIG. 2 depicts a high-level functional block diagram of a control unit 200 according to an embodiment. In at least some embodiments, control unit 200 may be used as control unit 124 (FIG. 1).

Control unit 200 comprises a processing device 202, an input/output (I/O) device 204, a memory 206, a phased array I/F 208, and an encoder I/F 210 each communicatively coupled via a bus 212 or other interconnection communication mechanism.

I/O device 204 may comprise an input device, an output device and/or a combined input/output device for enabling user interaction. An input device may comprise, for example, a keyboard, keypad, mouse, trackball, trackpad, and/or cursor direction keys for communicating information and commands to processing device 202. An output device may comprise, for example, a display, a printer, a voice synthesizer, etc. for communicating information to a user. In at least some embodiments, I/O device 204 may comprise a serial and/or parallel connection mechanism.

Memory 206 (also referred to as a computer-readable medium) may comprise a random access memory (RAM) or other dynamic storage device, coupled to the bus 212 for storing data and/or instructions to be executed by processing device 202. Memory 206 also may be used for storing temporary variables or other intermediate information during execution of instructions to be executed by processing device 202. Memory 206 may also comprise a read only memory (ROM) or other static storage device coupled to the bus 212 for storing static information and instructions for the processing device 202.

Memory 206 stores a rail scan control 214 (a set of executable instructions) for controlling interaction with the phased array probes 114 (FIG. 1) via phased array I/F 208. Memory 206 also stores scan settings 216 corresponding to particular scan settings of a particular scan performed by rail scanning system 102. For example, scan setting 216 comprises one or more items of calibration data related to rail scanning system 102 configuration.

Figure 10:
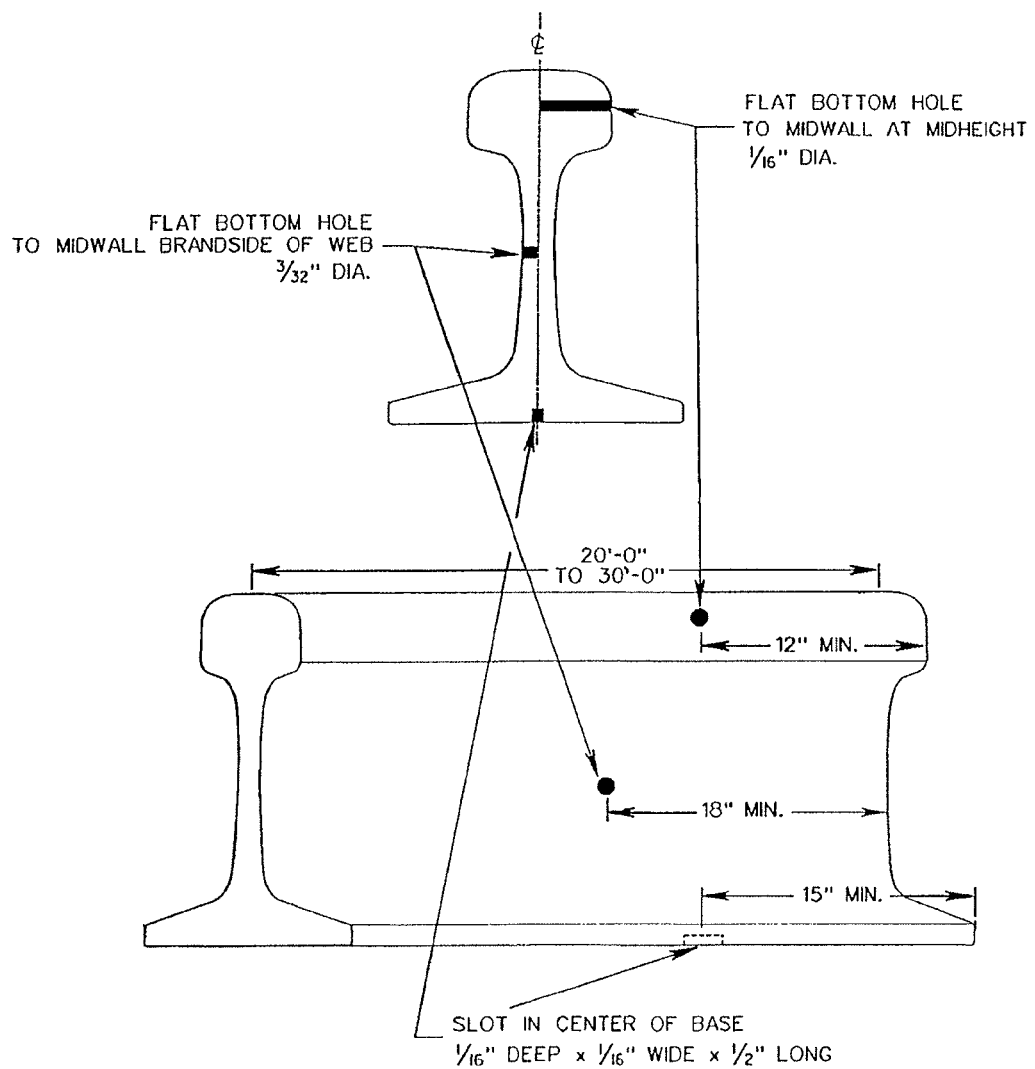
FIG. 10 is an ultrasonic reference rail diagram.

In particular, in at least some embodiments, rail scanning system 102 is calibrated for sensitivity using an ultrasonic rail reference rail depicted in FIG. 10. The reference rail includes known defects which are to be detected. Detection of the defects is used to calibrate the rail scanning system. Rail scanning system 102 gain (in decibels (db)) is adjusted to detect calibration references, as follows:

| Head | ³/₃₂" diameter hole, ¾ inch | 70° angle |
|---|---|---|
| Web | ⅛" wide × ½" long slot drilled to mid-wall of web | 45° angle |
| Base | ⅛" × ⅛" × 1" long slit milled in bottom of center of base | 0°, 45° angles |

In at least some embodiments, rail calibration settings, i.e., settings of rail scanning system 102 at which defects in the reference rail are detect, stored in scan settings 216 include measurement line, gain, range, and material velocity. The rail calibration settings stored at calibration time are later compared to scan settings 216 stored at the time of a scan to verify that rail scanning system 102 settings have not changed.

Memory 206 also stores a scan result 218 corresponding to received response signals from the phased array probes 114 via phased array I/F 208.

Memory 206 also stores a scan motion information 220 corresponding to a received motion signal from encoder 122 (FIG. 1).

Phased array I/F 208 comprises a communication interconnection mechanism for transmitting and receiving signals to/from the phased array probes 114 (FIG. 1). In at least some embodiments, phased array I/F 208 may comprise a wired and/or wireless connection mechanism.

Encoder I/F 210 comprises a communication interconnection mechanism for transmitting and receiving signals to/from encoder 122 (FIG. 1). In at least some embodiments, encoder I/F 210 may comprise a wired and/or wireless connection mechanism.

In at least some embodiments, control unit 200 comprises a mechanism for connecting to a network and/or computer system such as computer system 110 (FIG. 1). In at least some embodiments, control unit 200 comprises more than a single network interface. In at least some embodiments, control unit 200 may comprise a wired and/or wireless connection mechanism.

Figure 3:
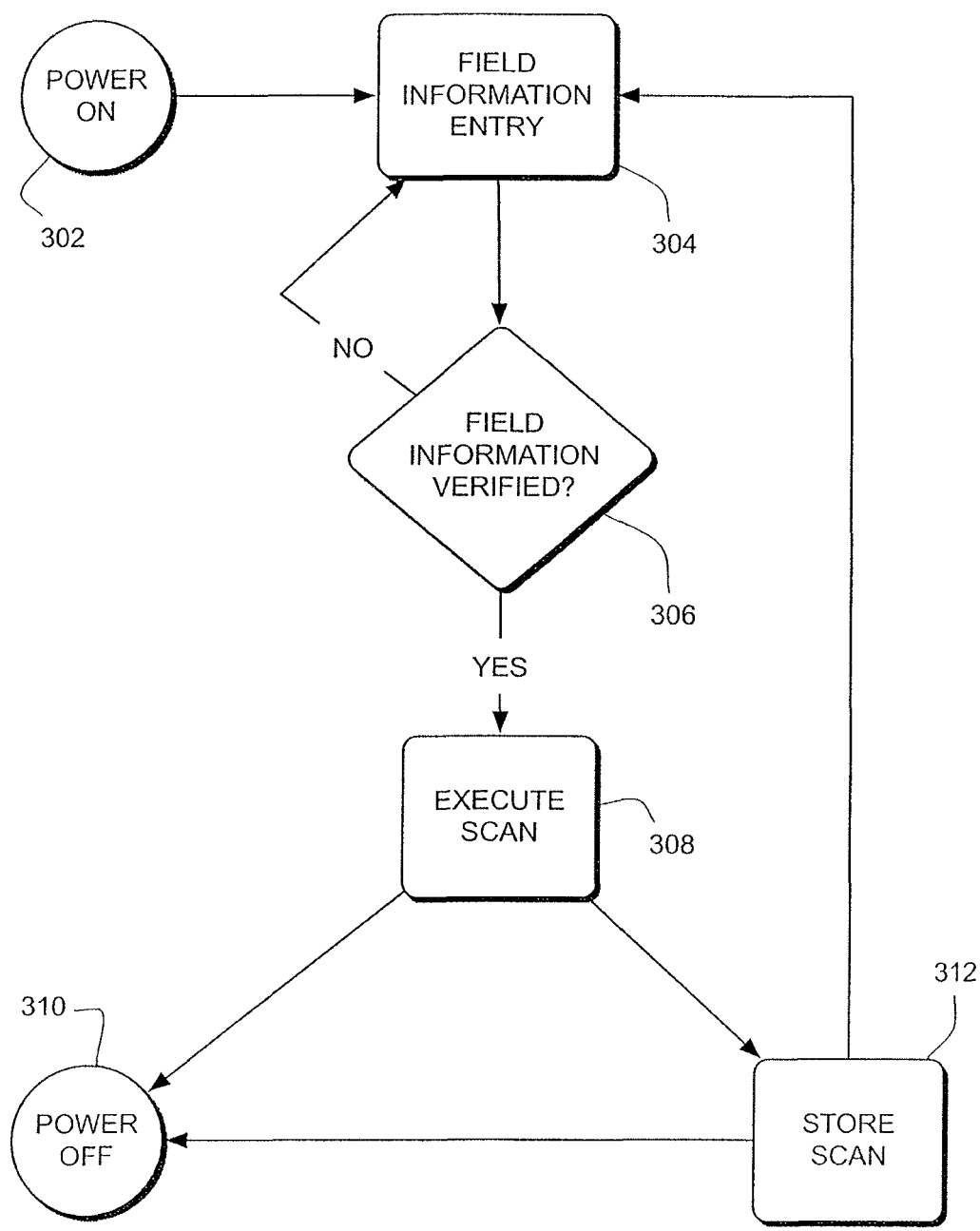
FIG. 3 is a high-level process flow diagram of at least a portion of rail scan control according to an embodiment.

FIG. 3 depicts a high-level process flow diagram of at least a portion of rail scan control 214 (FIG. 2) according to an embodiment when executed by processing device 202 of control unit 200. The process flow begins at power on functionality 302. After initial start up of control unit 200, the flow proceeds to field information entry functionality 304.

During execution of the set of instructions comprising field information entry functionality 304 by processing device 202, user input regarding at least a user identifier and a location identifying information are received by control unit 200, e.g., via I/O device 204 such as a touch screen or keypad/keyboard. In at least some embodiments, a display comprising I/O device 204 may prompt the user for the required information.

In at least some embodiments, a dialog display is presented to the user via I/O device 204 prompting the user to supply and/or verify the required information. FIG. 4 depicts an exemplary dialog display 400 according to an embodiment.

Subsequent to receipt of the required information, the flow of control proceeds to verification functionality 306 wherein execution of a set of instructions by processing device 202 causes the processing device to verify the receipt of entries for each of the required fields of information. In at least some embodiments, the entered information may be verified with additional information, e.g., a location information may be verified through the use of geo-location input such as from a wireless network and/or a geo-positioning mechanism such as a global positioning system (GPS).

If the result of verification functionality 306 is negative ("NO"), the flow returns to field information entry functionality 304 and the user may be again prompted to enter the required information and/or correct previously entered information.

If the result of verification functionality 306 is positive ("YES"), the flow proceeds to execute scan functionality 308 wherein the scan of rail may be performed by a user using the phased array probes 114 (FIG. 1). In at least some embodiments, execution of scan functionality 308 causes display of information to the user indicating that the rail scanning system 102 is prepared to begin scanning.

Subsequent to completion of scanning, the user may decide to power off rail scanning system 102 without saving the scan result. The flow then proceeds to power off functionality 310.

Also, subsequent to completion of scanning, the user may decide to store the scan result, e.g., as a scan result 218 (FIG. 2). The scan result stored comprises the received response signals from phased array probe jig 114 (FIG. 1). In at least some embodiments, the scan result stored comprises at least one image resulting from analysis of the received response signals. The flow then proceeds to store scan functionality 312 wherein execution of a set of instructions by processing device 202 causes the processing device to store the received response signals to scan result 218 in memory 206. In at least some embodiments, execution of store scan functionality 312 also causes the processing device to store the received motion signal to scan motion 220 of memory 206 and to store the scan settings of rail scanning system 102 to scan settings 216 of memory 206. In at least some embodiments, storage of scan result 218 requires storage of scan settings 216 corresponding to the settings during the scan resulting in the scan result.

Subsequent to completion of store scan functionality 312, the flow may proceed to either power off functionality 310 or field information entry functionality 304. In at least some embodiments, the flow proceeds based on a user input. In at least some embodiments, the flow proceeds automatically based on a predefined setting.

Figure 5:
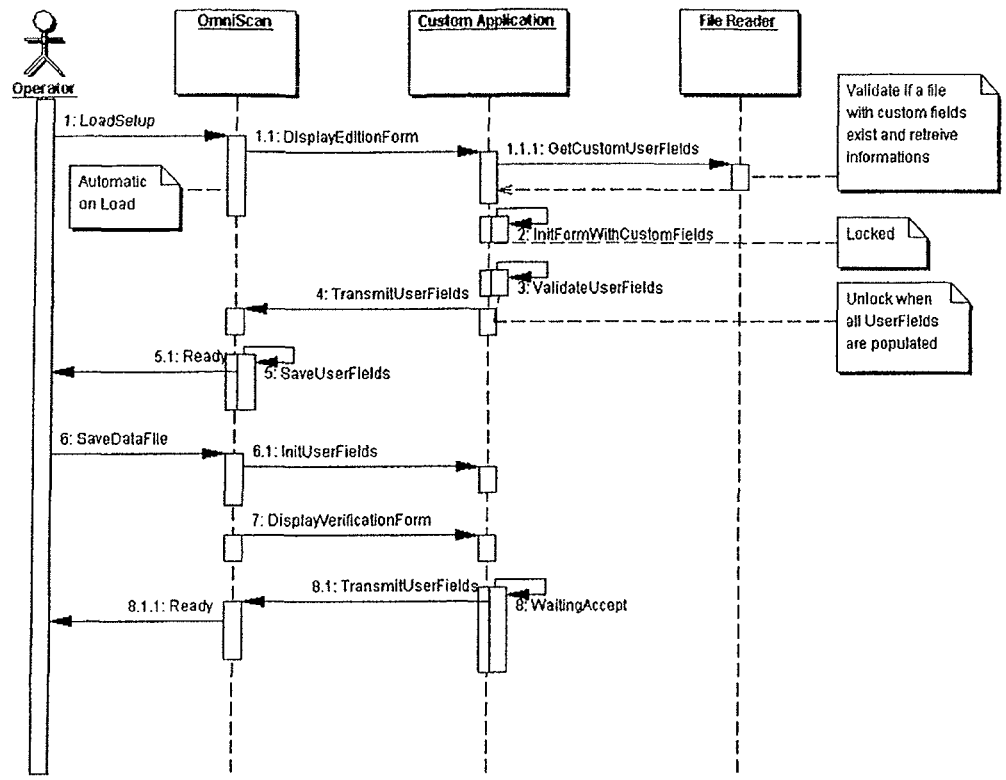
FIG. 5 is a high-level message sequence flow diagram of operation of at least a portion of a rail scan control according to an embodiment.

FIG. 5 depicts a high-level message sequence flow diagram of operation of at least a portion of rail scan control 214 according to an embodiment.

Figure 6:
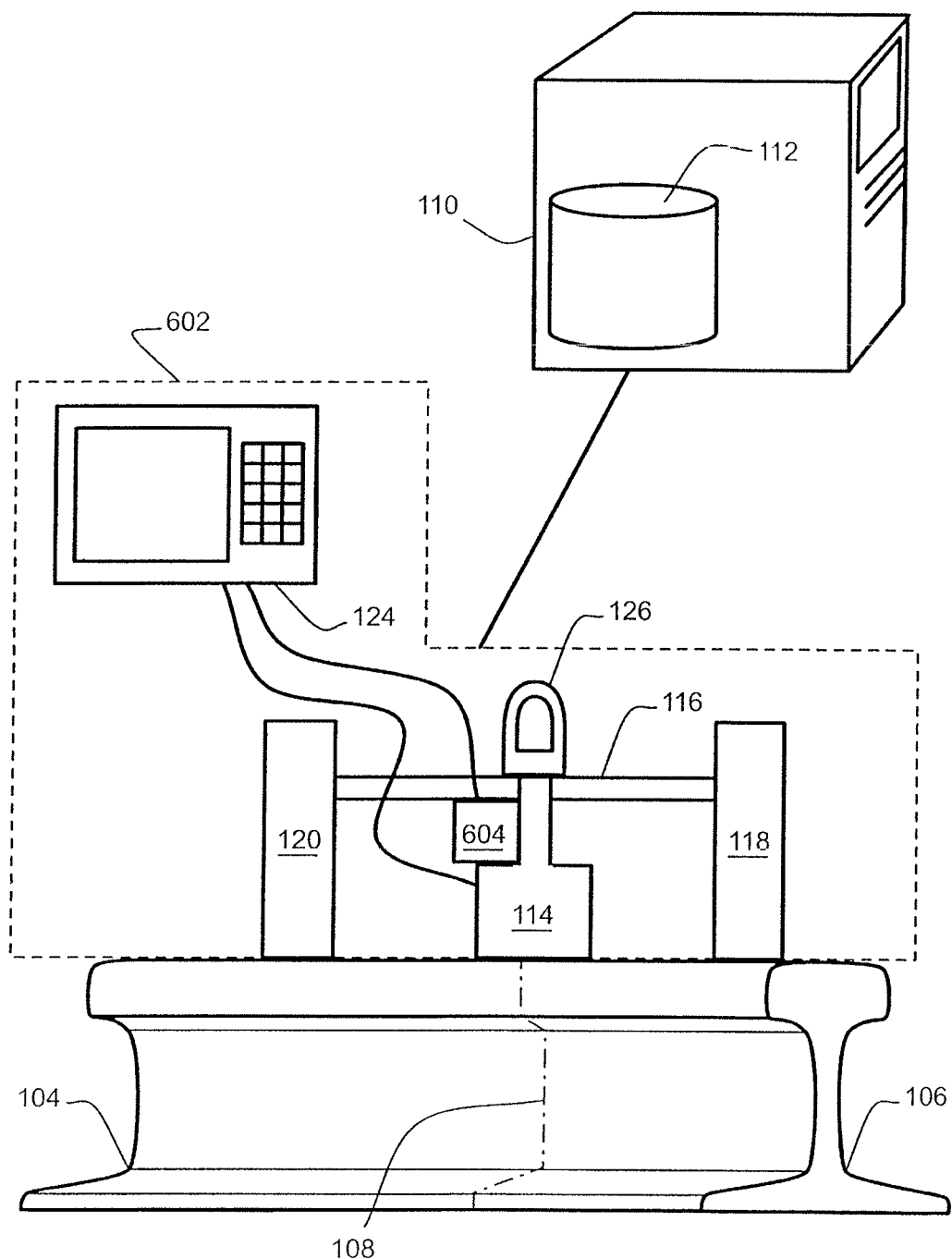
FIG. 6 is a high-level block diagram of an environment for using a rail scanning system according to another embodiment.

FIG. 6 depicts a high-level block diagram of an environment 600 for using a rail scanning system 602 according to another embodiment. Environment 600 is similar to environment 100 (FIG. 1) and rail scanning system 602 is similar to rail scanning system 102 (FIG. 1). Rail scanning system 602 differs from rail scanning system 102 by using a different encoder 604 located adjacent to the phased array probe carriage 114 for generating a motion signal corresponding to movement of the phased array probe carriage along guide unit 116. For example, encoder 604 may comprise a rotary encoding wheel in contact with guide unit 116.

Figure 7:
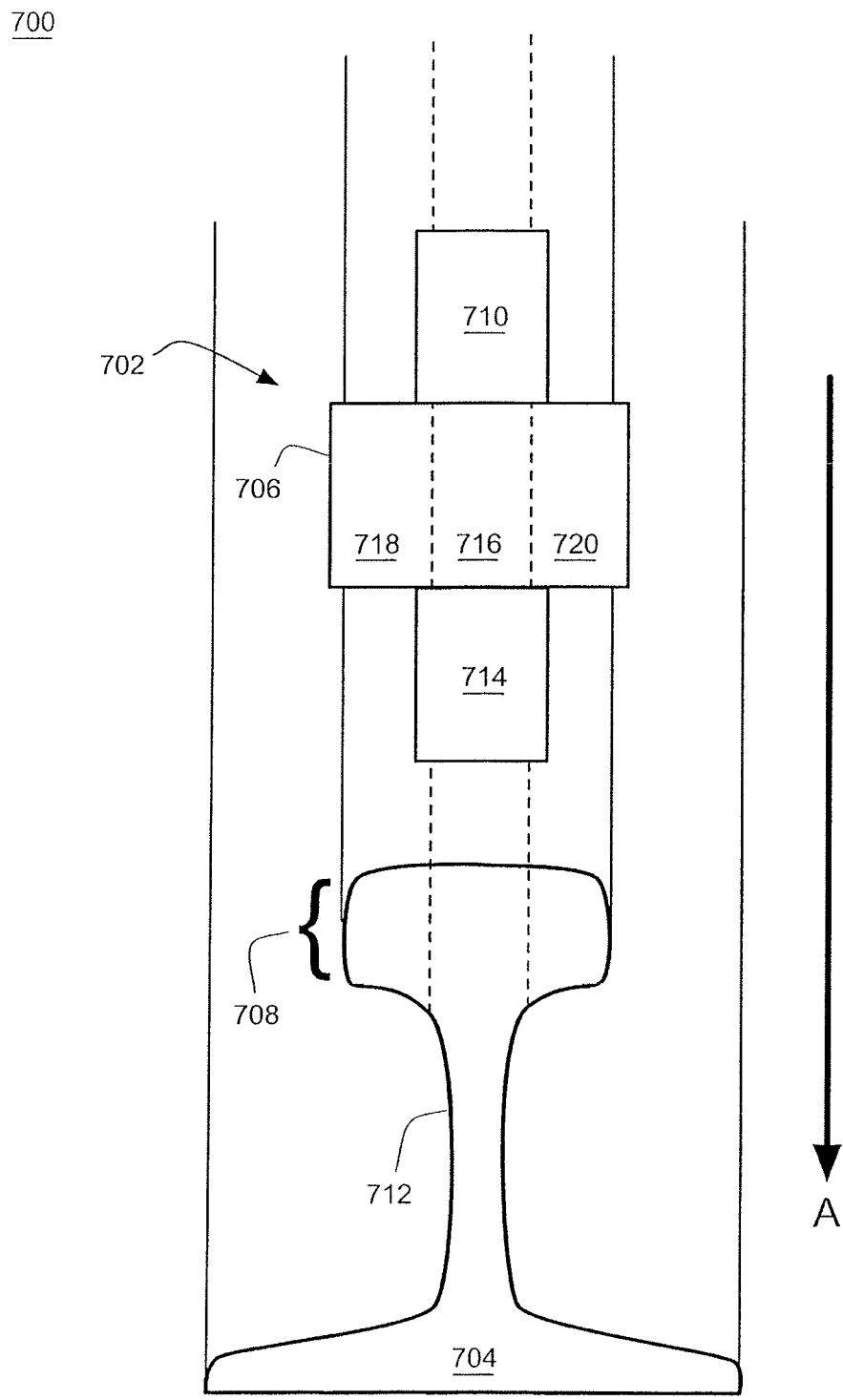
FIG. 7 is a top representational view of an environment comprising a phased array unit according to an embodiment.

FIG. 7 depicts a top representational view of an environment 700 comprising a phased array probe jig 702 atop the head portion of a rail segment 704 extending vertically along the page in a direction A. For clarity and ease of reference, connections and portions of other components of rail scanning system 102 have been omitted.

Rail segment 704 may comprise a portion of rail 104 or a portion of rails 104, 106. (FIG. 1)

Phased array probe carriage 702 is one embodiment of phased array probe carriage 114 (FIG. 1). In at least some other embodiments, different sizes, shapes and/or orientation of components of or the entirety of phased array probe carriage 702 may be used.

Phased array probe carriage 702 comprises three phased array probes (also referred to as probes) 706, 714, and 710. Each probe is connected to control unit 124 and transmits received response signals to the control unit responsive to transmission of a signal toward rail 704 at multiple angles. In at least some embodiments, the angles are transmitted from control unit 124 to each of the probes.

A central probe unit 706 extends across a head portion 708 of rail 704. In at least some embodiments, central probe 706 extends slightly beyond head portion 706 width. A forward probe 710 is positioned adjacent one end of central probe 706 and extends across a central region of head portion 708 (indicated by dashed line). In at least some embodiments, forward probe 710 extends slightly beyond central region width. In at least some embodiments, the central region width corresponds to a region as wide as a web portion 712 of rail 704.

A rearward probe 714 is positioned adjacent an opposite end of central probe 706 from forward probe 710 and extends across a central region of head portion 708. In at least some embodiments, rearward probe 714 extends slightly beyond central region width.

Central probe unit 706 comprises three sub-sections linearly positioned adjacent each other from left to right across head portion 708: a central sub-section 716, a left sub-section 718, and a right sub-section 720.

Figure 8A:
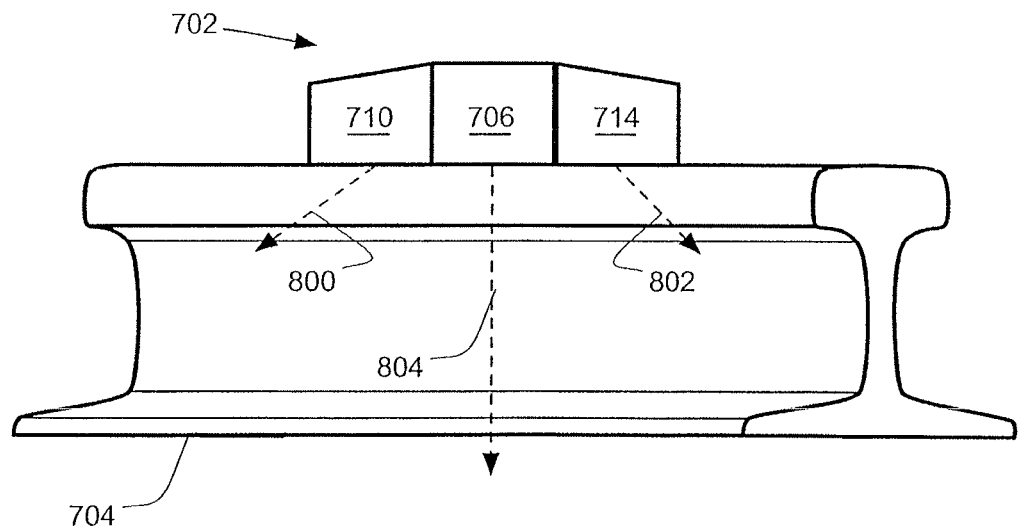
FIGS. 8A and 8B are a side view and a cross-section view, respectively, of a phased array unit according to an embodiment.
Figure 8B:
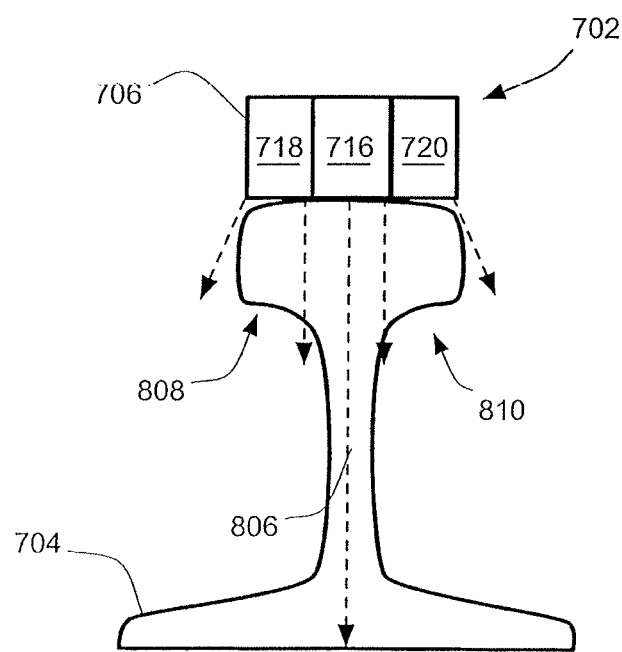

FIGS. 8A and 8B depict a side view of the phased array probe carriage 702 and a front cross-section view of the phased array probe carriage positioned atop rail 704, respectively. As depicted in FIG. 8A, forward probe 710 and rearward probe 714 each transmit a signal (indicated by dashed lines 800, 802, respectively) into rail 704 at multiple angles from seventy degrees) (70°) to thirty-five degrees (35°) from vertical. As depicted, the transmitted signals are transmitted into rail 704 at opposing angles along the length of the rail in order that opposing views may be obtained by a single scan. Also, central probe 706 transmits signals (indicated by dashed line 804) into rail 704 at multiple angles along the width of the rail from vertical. The signal transmitted by central probe 706 is transmitted sufficient to obtain a response signal from the top of rail 704 (at the head portion) to the base of the rail (toward the bottom of the page).

As depicted in FIG. 8B, central sub-section 716 of central probe 706 transmits multiple signals into rail 704 at an angle of zero degrees (0°) from vertical (indicated by dashed line 806). The signal transmitted by central sub-section 716 is transmitted sufficient to obtain a response signal from the top of rail 704 (at the head portion) to the base of the rail (toward the bottom of the page).

Also, as depicted in FIG. 8B, left sub-section 718 and right sub-section 720 each transmit multiple signals into rail 704 from vertical (the area bounded by dashed lines and indicated generally by reference numerals 808 and 810, respectively). As depicted, the transmitted signals are transmitted into rail 704 at divergent angles from each other so that the entire head portion of rail 704 may be imaged.

Figure 9:
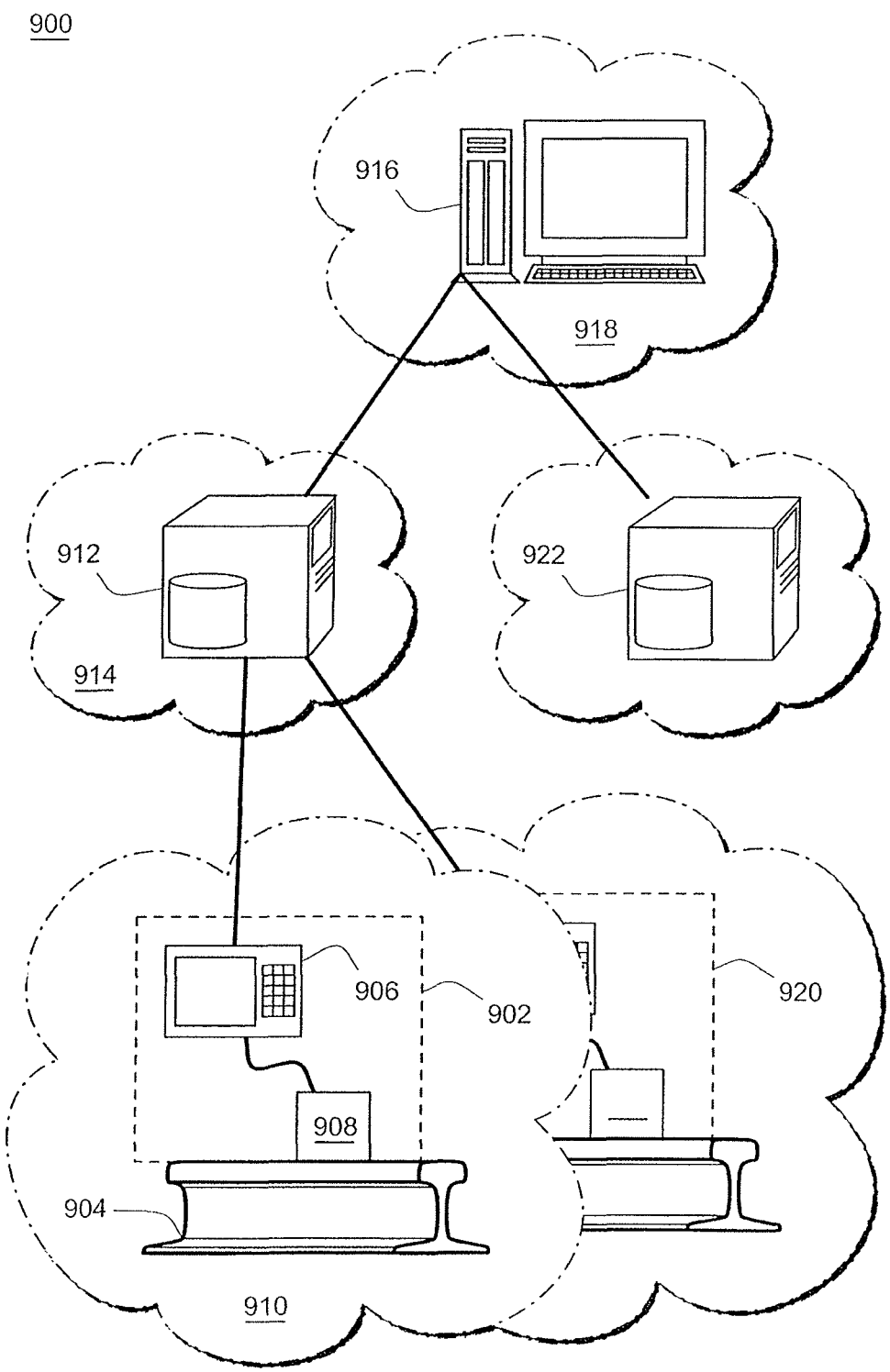
FIG. 9 is a high-level block diagram view of a network usable in conjunction with an embodiment.

FIG. 9 depicts a certification environment 900 in conjunction with which an embodiment may be practiced. In particular, a rail scanning system 902 (similar to rail scanning system 102 described above in connection with FIG. 1) is positioned above a rail 904 and comprises a control unit 906 and a rail scanner 908 communicatively coupled with each other (corresponding to control unit 124 and rail scanner 113). Rail scanning system 902 is controlled by a user located at a particular region 910.

Rail scanning system 902 at region 910 is communicatively coupled to a field computer system 912 (similar to computer system 110 of FIG. 1) located at a particular region 914. In at least some embodiments, the user of rail scanning system 902 may transport all or a portion of the rail scanning system between particular regions 910 and 914. In at least some embodiments, a wired and/or wireless connection may be established to transfer information between rail scanning system 902 and field computer system 912. In at least some embodiments, particular region 914 may be a field office.

Field computer system 912 at region 914 is, in turn, communicatively coupled to a central computer system 916 at a particular region 918. In at least some embodiments, particular region 918 is a centralized office location. In at least some embodiments, central computer system 916 is similar to computer system 110 of FIG. 1. Central computer system 916 may be connected with field computer system 912 via either wired and/or wireless network connections. In at least some embodiments, a user at field computer system 912 may physically transfer memory having at least a portion of scan settings 216, scan result 218, and scan motion 220 from the field computer system to central computer system 916. In at least some embodiments, central computer system 916 may store rail calibration settings related to rail scanning system 902 in memory local to the central computer system.

FIG. 9 depicts an additional rail scanning system 920 connected with field office computer system 912, as well as, an additional field office computer system 922 connected with central computer system 916. In this manner, more than a single rail scanning system and more than a single field office computer system may comprise certification environment 900.

In operation, prior to the user using rail scanning system 902, the rail scanning system is calibrated and the rail calibration settings stored in memory 206 of control unit 124. In at least some embodiments, the rail calibration settings are stored in one or more of field computer system 912 and/or central computer system 916.

Rail Calibration and storage of rail calibration settings may be performed by a user having a different set of privileges and/or authorization, e.g., an administrator, than the user performing the scan of rail at particular region 910.

The user performing the scan of the rail at particular region 910 positions rail scanning system 902 on the rail and activates the rail scanning system, in particular the control unit 906. Consistent with the flow described in conjunction with FIG. 3, the user is prompted to input entries for one or more fields of information related to the scan, e.g., as in the dialog of FIG. 4. In at least some embodiments, entry of valid information by the user into each field is required prior to enabling a scan to be performed. In at least some other embodiments, entry of valid information by the user into each field is required prior to enabling the user the store the scan results.

In at least some embodiments, storage of scan results additionally results in storage of the current scan settings, i.e., rail scanning system 102 settings for the most recent scan performed, and the scan motion information.

After completion of a scan, the scan results, scan settings, and scan motion information is transferred from control unit 906 to field computer system 912 by the user. Subsequent to the transfer from control unit 906, the scan results, scan settings, and scan motion information is transferred from field computer system 912 to central computer system 916. In at least some embodiments, transfer of the scan results, scan settings, and scan motion information occurs using one or more of a wired and/or wireless network connection.

After transfer of the scan results, scan settings, and scan motion information to central computer system 916, another user, e.g., different from the user of rail scanning system 102 such as an analyst, is able to review the scan results. Using the scan settings, the analyst is able to verify that the scan was performed using a calibrated rail scanning system by comparison with prior stored versions of calibration information for the particular rail scanning system 102, e.g., stored in memory local to central computer system 916. In this manner, an end-to-end certification of rail scans may be performed using a rail scanning system according to an embodiment.

It will be readily seen by one of ordinary skill in the art that the disclosed embodiments fulfill one or more of the advantages set forth above. After reading the foregoing specification, one of ordinary skill will be able to affect various changes, substitutions of equivalents and various other embodiments as broadly disclosed herein. It is therefore intended that the protection granted hereon be limited only by the definition contained in the appended claims and equivalents thereof.

What is claimed is:

1. A rail scanning system comprising:
   a control unit arranged to generate one or more phased array signals;
   a probe carriage arranged to move along a rail and comprising:
   two or more phased array probes, including a forward probe, a central probe, and a rearward probe, each communicatively coupled with said control unit and each arranged to transmit at least one of the generated phased array signals; and
   an encoder coupled with said probe carriage and arranged to generate one or more motion signals responsive to movement of said probe carriage wherein at least one of said forward probe and said rearward probe is arranged to transmit the generated phased array signals at angles sweeping between seventy degrees and thirty-five degrees from vertical into a rail.

2. The rail scanning system of claim 1, wherein the two or more phased array probes are each arranged to transmit a received response signal to said control unit responsive to transmission of the at least one of the generated phased array signals.

3. The rail scanning system of claim 2, wherein the phased array probes are each arranged to transmit the received response signal responsive to transmission of the generated phased array signals concurrently.

4. The rail scanning system of claim 1, further comprising:
   a guide unit movably coupling said probe carriage to said encoder.

5. The rail scanning system of claim 4 wherein said guide unit comprises a threaded segment cooperatively coupled with said probe carriage and said encoder.

6. The rail scanning system of claim 4, further comprising:
   a pair of end pieces each connected with said guide unit and positioned toward opposite ends of said guide unit.

7. The rail scanning system of claim 6, wherein at least a portion of said pair of end pieces are magnetic.

8. The rail scanning system of claim 1, wherein said forward probe is arranged to transmit at least one of the generated phased array signals at an angle between seventy degrees and thirty-five degrees from vertical into a rail.

9. The rail scanning system of claim 1, wherein said rearward probe is arranged to transmit at least one of the generated phased array signals at an angle between seventy degrees and thirty-five degrees from vertical into a rail.

10. The rail scanning system of claim 1, wherein said central probe is arranged to transmit at least one of the generated phased array signals at an angle zero degrees from vertical into a rail.

11. The rail scanning system of claim 1, wherein said central probe comprises at least two sub-sections each arranged to generate at least one of the generated phased array signals at an angle into a rail.

12. The rail scanning system of claim 1, wherein the control unit is configured to:
   store first rail calibration settings responsive to second user input information identifying the user as having a different set of privileges than first user input information.

13. The rail scanning system of claim 12, wherein the control unit is further configured to:
   verify the stored scan result based on a comparison of the first rail calibration settings with the second rail calibration settings.

14. The rail scanning system of claim 12, wherein the stored first rail calibration settings comprise at least one of a measurement line, a gain, a range, or a material velocity.

15. The rail scanning system of claim 12, wherein the user input information comprises at least a user identifier or a rail scanning location.

16. A method of certifying a rail scan performed by a rail scanning system, comprising:
   storing first rail calibration settings of the rail scanning system;
   receiving user input information at the rail scanning system;
   enabling scanning a rail using the rail scanning system responsive to verification of the received user input information at the rail scanning system; and
   storing the result of scanning the rail and second rail calibration settings of the rail scanning system, wherein receipt of the user input information at the rail scanning system is required prior to enabling storing the result of scanning the rail.

17. A method of certifying a rail scan performed by a rail scanning system, comprising:
   storing first rail calibration settings of the rail scanning system;
   receiving first user input information identifying a first user at the rail scanning system;
   enabling scanning a rail using the rail scanning system responsive to verification of received first user input information at the rail scanning system; and
   storing the result of scanning the rail and second rail calibration settings of the rail scanning system, wherein the storing first rail calibration settings of the rail scanning system is responsive to second user input information identifying the user as having a different set of privileges than the first user input information.

* * * * *